(12) United States Patent
Durner et al.

(10) Patent No.: US 6,562,108 B2
(45) Date of Patent: May 13, 2003

(54) STACK LIQUID SEPARATOR AND METHOD OF USE

(75) Inventors: Michael W. Durner, Powell, OH (US); Scott J. Kutzley, Worthington, OH (US)

(73) Assignee: AEP Emtech, LLC, Columbus, OH (US)

(*) Notice: Subject to any disclaimer, the term of this patent is extended or adjusted under 35 U.S.C. 154(b) by 0 days.

(21) Appl. No.: 09/967,412

(22) Filed: Sep. 27, 2001

(65) Prior Publication Data

US 2002/0083834 A1 Jul. 4, 2002

Related U.S. Application Data

(60) Provisional application No. 60/235,800, filed on Sep. 27, 2000.

(51) Int. Cl.[7] ............................................. B01D 45/12
(52) U.S. Cl. ......................... 95/269; 55/318; 55/419; 55/447; 55/457; 55/465
(58) Field of Search ............................. 55/337, 385.1, 55/418, 419, 444, 462, 465, 447, 459.1, 318, 457; 95/269, 271, 272

(56) References Cited

U.S. PATENT DOCUMENTS

| | | |
|---|---|---|
| 3,348,364 A | 10/1967 | Henby |
| 3,543,485 A | 12/1970 | Hardison |
| 3,772,856 A | 11/1973 | Moran |
| 4,080,186 A | 3/1978 | Ockert |
| 4,254,758 A * | 3/1981 | Banks ........................ 126/247 |
| 4,322,233 A | 3/1982 | Sisk |
| 5,201,919 A | 4/1993 | Jahn et al. |
| 5,885,333 A | 3/1999 | Dix |

FOREIGN PATENT DOCUMENTS

| | | |
|---|---|---|
| JP | 02 033515 A | 4/1990 |
| JP | 09 229346 A | 1/1998 |

OTHER PUBLICATIONS

Mitsubishi Chimney Publication (Undated but believed to have been published Nov. 1997).
Burns & McDonnell Engineering Company, Wet Stacks Designb Guide Nov. 1996.

* cited by examiner

Primary Examiner—Robert A. Hopkins
(74) Attorney, Agent, or Firm—Sand & Sebolt

(57) ABSTRACT

A method of removing a liquid entrained in a gas moving at a velocity in an upward direction from a base to a top of a stack comprising the steps of imparting a swirling direction to the velocity of the gas adjacent the base of the stack and then recovering at least some of the liquid adjacent the top of the stack. Also disclosed is an apparatus for removing a liquid entrained in a gas in a stack having a base and a top comprising at least one duct having a longitudinal axis entering the stack adjacent said base and at least one vertical vane disposed at and angled to the longitudinal axis of the duct and a collector adjacent the top of the stack for recovering liquid.

42 Claims, 10 Drawing Sheets

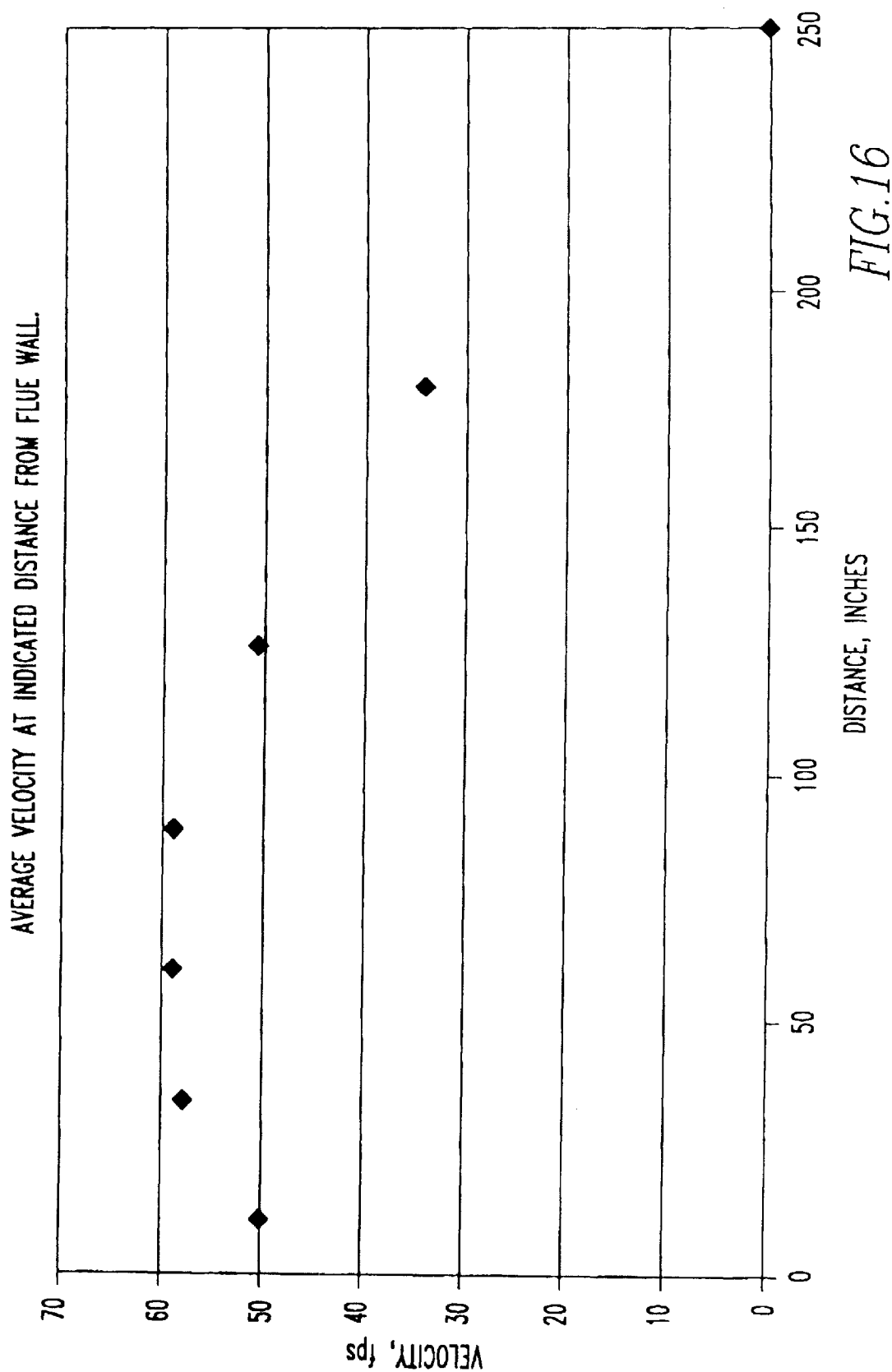

STACK LIQUID SEPARATOR AND METHOD OF USE

BACKGROUND OF THE INVENTION

1. Technical Field

The present invention relates to stacks for the removal of combustion products and more particularly, to methods and apparatus for removing liquid from liquid and gas mixtures in such stacks. Still more particularly, this invention relates to the removal of liquids from gasses entrained in stacks of wet scrubbed coal fired electrical generating plants.

2. Background Information

The prior art discloses various apparatus and methods for separating entrained liquids from a gas stream in stacks and other locations.

U.S. Pat. No. 3,348,364 to Henby, for example, discloses a wet type, updraft gas scrubber comprising a vertical cylindrical housing with inlet means adjacent the lower end and outlet means adjacent the upper end, a filter bed extending transversely across the housing intermediate the inlet and outlet comprising a plurality of spherical filter elements, liquid spray means for introducing fine liquid droplets into the gas flowing upwardly into the filter bed to wet and collect contaminants in the gas, separator means intermediate said filter bed and the outlet for removing and collecting any liquid or mist remaining in the gas flowing upwardly from said filter bed, said separator means including a pair of rings defining an annular flow path substantially smaller in cross section than the housing for accelerating the gas flow therethrough and a plurality of adjustable deflecting vanes mounted between said rings in said flow path for directing the high velocity, upwardly flowing gas outwardly with a horizontal component against the housing wall, an annular liquid collecting trough between the outer ring and said housing wall for collecting liquid centrifuged outwardly against the wall, and drain means for said trough directing the collected liquid onto said filter bed.

U.S. Pat. No. 3,543,485 to Hardison discloses a vessel wall cooperating with a circular array of moisture separators which have a vertical riser tube, centrally disposed hubs, a vertical baffle disposed between the hub and the riser tube, turning vanes and an outer volute partial skirt or wall to compress the steam-water mixture against the volute and vessel wall and utilize the downwardly spiraling flow of liquid film formed on the volute and vessel wall to effectively separate the entrained water from the steam and prevent re-entrainment thereof.

U.S. Pat. No. 4,322,233 to Sisk discloses vertically aligned centrifugal particle separator wherein a multiplicity of static vanes extend upward from and are circumferentially fixed around a static spinner. The spinner has a hub and blades and is axially mounted over a particle laden gas inlet. A gas stream rising from the gas inlet is forced into an ascending spiral by the spinner blades. Relatively dense particles entrained in the gas stream are thrown centrifugally outward and are either passed between static vanes or strike static vanes, and in either case are deflected into a particle receiving section, which is the space bounded by the outer surfaces of the gas inlet and the static vanes and the inner surface of the centrifugal particle separator.

U.S. Pat. No. 5,201,919 to John, et al. discloses a gas scrubbing device having inlet and outlet ports that allows a gas stream to enter the scrubber from the bottom and exit through the top. The gas direction is reversed several times, fed through a venturi to accelerate the gas flow, and passed over two sumps containing scrubbing liquid. The combination of the high speed gas flow, gas flow reversal, and scrubbing liquid removes most particulates from the gas. The gas flows upward through a mist of scrubbing liquid created by a spray nozzle, and as the gas flows beyond the mist it flows through a series of serpentine vanes which cause the gas to change direction flow removing additional liquid droplets from the gas, through a reducing element, and out through the outlet port.

A need still exists, however, to improve the efficiency of liquid removal from gas entrained in stacks.

A need also exists for an improved means for preventing liquid droplets from falling from stack planes in areas adjacent the stack.

SUMMARY OF THE INVENTION

An object of the present invention is to provide an easy, inexpensive and efficient method and apparatus for separating liquid entrained in a gas stream in particularly of an existing stack, or new stack.

Another object of the present invention is to provide an improved method and apparatus for preventing liquid droplets from falling from stack planes in areas adjacent the stack.

The above objects are accomplished by the present invention which is a method and apparatus for imparting a swirling velocity component to a gas flow in a stack and then collecting entrained liquid droplets at the top of the stack. The apparatus used to impart this swirling motion comprises a plurality of parallel vertical vanes positioned in front of ducts at the base of the stack. As gas flows inwardly through the ducts to the stack, it encounters the vanes which are positioned at a selected preferred angle to impart the desired swirl.

BRIEF DESCRIPTION OF THE DRAWINGS

The preferred embodiment of the invention, illustrative of the best mode in which applicant contemplated applying the principles, is set forth in the following description and is shown in the drawings and is particularly and distinctly pointed out and set forth in the appended claims.

FIG. 16 is a graph showing average velocity at the indicated distance from the flue wall for the example described herein.

DESCRIPTION OF THE PREFERRED EMBODIMENTS

Figure 1:
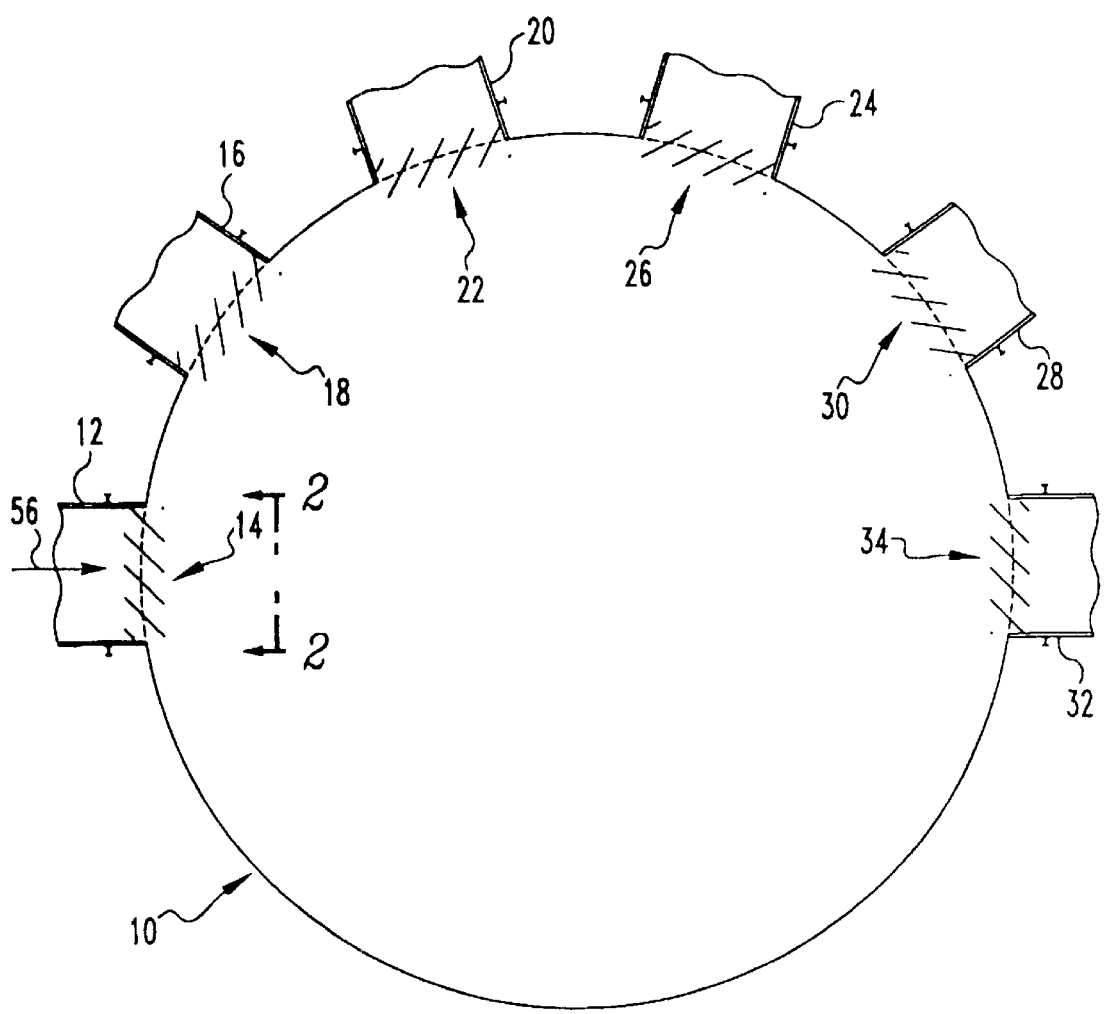
FIG. 1 is a schematic horizontal cross sectional view of a stack which embodies a preferred embodiment of the apparatus of the present invention.
Figure 2:
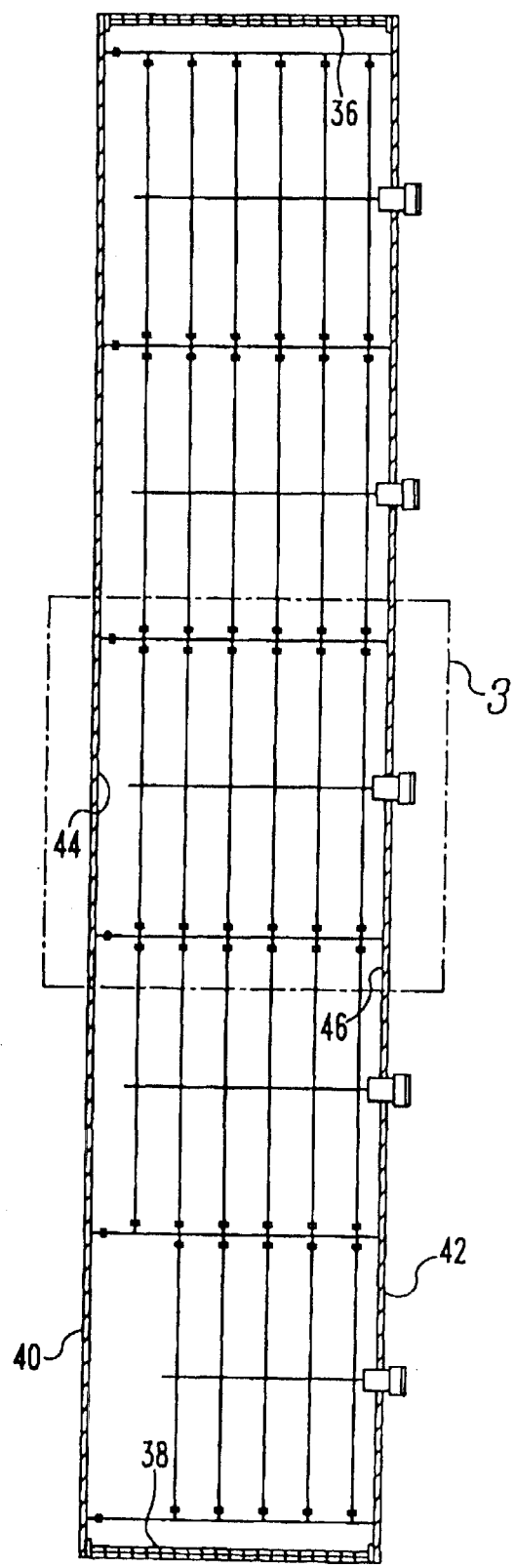
FIG. 2 is a view from 2—2 in FIG. 1 showing the stack reaching duct turning vanes feature of the apparatus of the present invention.

Referring to FIGS. 1–8, a stack shown generally at numeral 10 has a plurality of ducts, including duct 12 which is equipped with a plurality of vertical vanes 14 at the point which adjoins stack 10. Another duct 16 is similarly equipped with vertical vanes 18. There is another duct 20 having vertical vanes 22, another duct 24 having vertical vanes 26, another duct 28 having vertical vanes 30 and another duct 32 having vertical vanes 34. The duct has a top wall 36 and a base wall 38 and parallel elongated vertical sidewalls 40 and 42. On the sidewalls 40 and 42, there is a refractory block liner 44 and 46 respectively. The plurality of vanes as at vane 14 is made up of individual vertical vanes as at vanes 48 and 50. These vanes are angularly mounted on horizontal frames as at horizontal frames 52 and 54 at an angle with respect to the axis 56 of duct 12. Preferably this angle a will be between about 15° to about 35° and more preferably will be about 25°. The vertical vanes as at vanes 48 and 50 are stiffened with one or more horizontal rods as at rod 58 which is mounted on a bent plate as at plate 60 to a metallic can liner 62 on the interior of the stack 10. The ducts are also equipped with stiffeners as at stiffener 64. The angle of the vanes 48 and 50 with respect to the axis 56 of the duct 12 may be adjusted by removing the vanes 48 and 50 and frames 52 and 54 and reinserting the vanes 48 and 50 on different frames.

Those skilled in the art will appreciate that there are equivalent means for imparting a swirling direction to the gas stream in the stack. For example, instead of using a radially oriented duct with vanes angularly disposed to the longitudinal axis of the duct, it would be possible to use a duct which is positioned so that its longitudinal axis is oriented in a non-radial or tangential with relation to the stack. For the purposes of this disclosure the term "non-radial" will be considered to encompass any tangential or other direction in which the longitudinal axis of such a duct intersects a radius of the stack. Another equivalent means of generating a swirling direction to the gas stream would be by means of a fixed impeller positioned at the base or elsewhere in the stack. The use of such an impeller is further described hereafter.

Referring to FIGS. 9–12, the stack cap collector feature of the present invention makes use of the outer concrete stack shell 66 and the brick liner 68 of the stack. This feature includes support angles 70 on which a cap 72 is superimposed and attached by means of a bolt 74. A fiberglass reinforced plastic (FRP) collector lower gutter section 76 is superimposed over the cap 72. The brick liner 68 and an FRP upper roof section 78 is superimposed over this lower section 76. A moisture drain 80 extends downwardly from this lower section gutter 76 and through the cap 72 and support angle 70.

Figure 11:
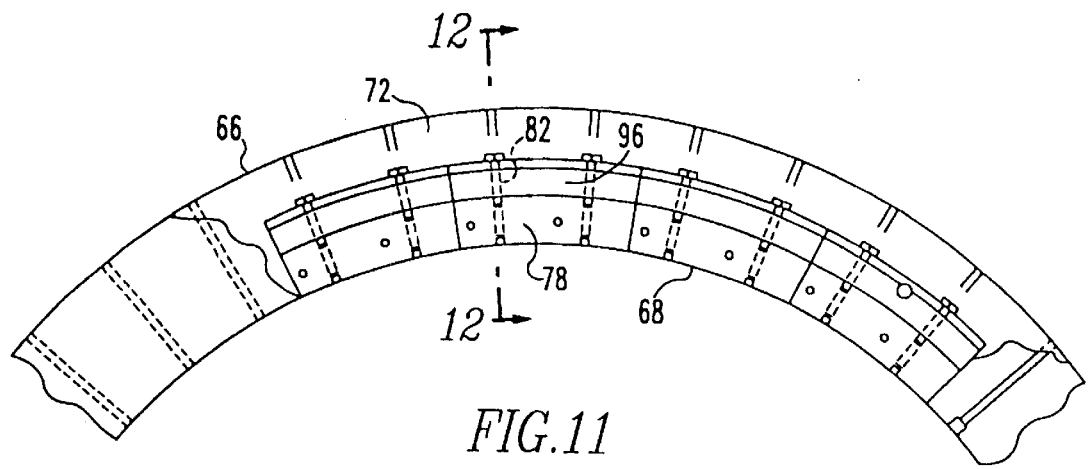
FIG. 11 is a top plan view of part of the stack shell and liner of the stack cap collector shown in FIGS. 9–10.
Figure 12:
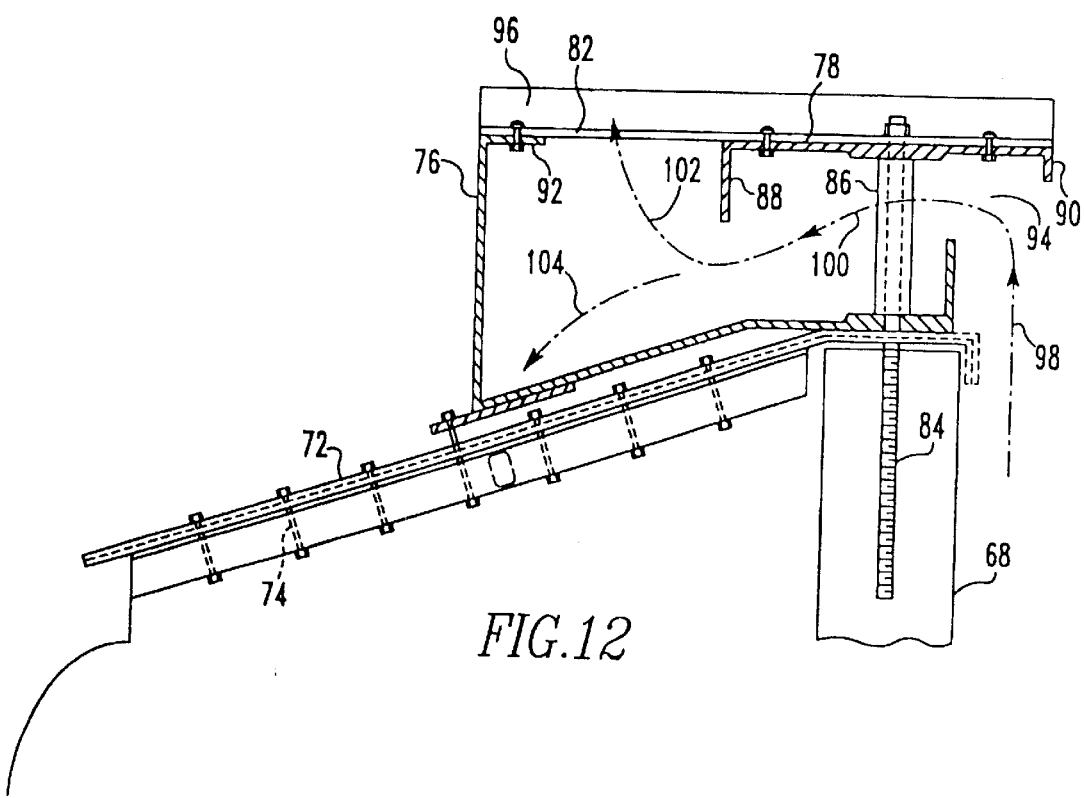
FIG. 12 is a cross sectional view through 12–12 in FIG. 11.

Referring particularly to FIGS. 11–12, a plurality of horizontal supports at support 82 extends between lower section gutter 76 and upper section roof 78. These horizontal supports as at support 82 would be mounted to the inner brick liner 68 by means of an anchor bolt 84 which is equipped with a spacer 86 which extends vertically between the FRP collector lower section gutter 76 and the FRP collector upper section roof 78. It will also be seen that there are downwardly extending flanges 88 and 90 on the outer and inward edges respectively of upper roof section 78. There is also an inwardly extending flange 92 form the outer side of the lower gutter section 76. The is also an inner opening 94 between the lower getter section 76 and upper roof section 78 and an upper opening 96.

Figure 10:
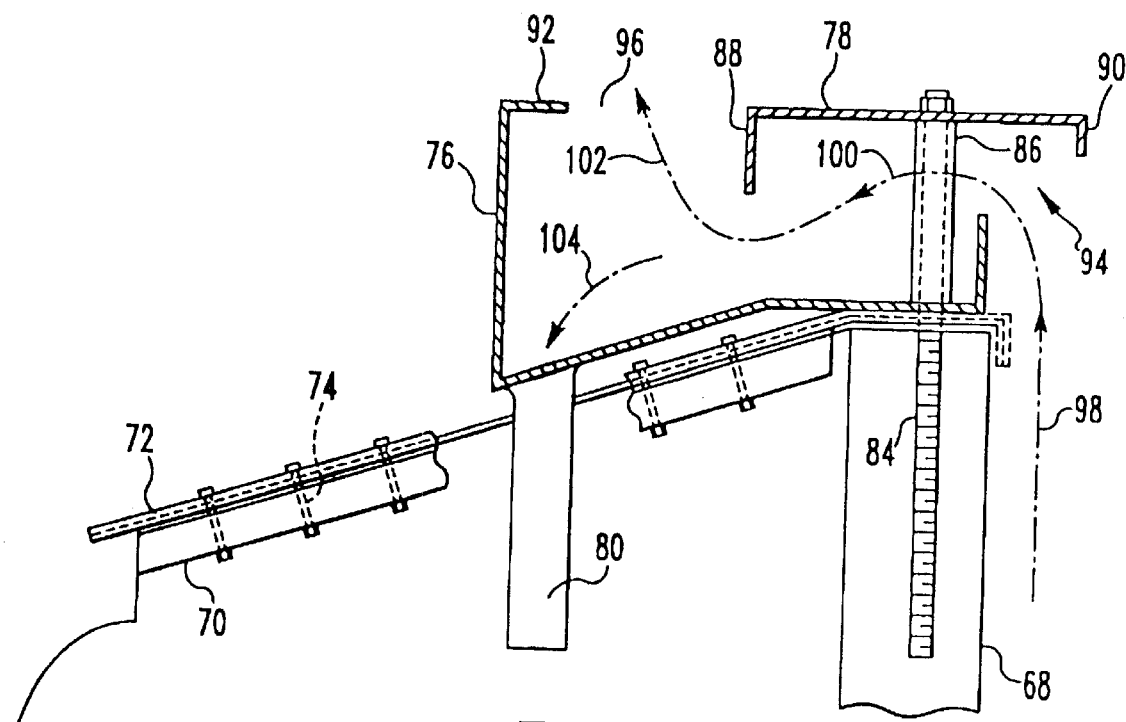
FIG. 10 is a detailed view of area 10 in FIG. 9.

Referring particularly to FIGS. 10 and 12, a gas stream with entrained liquid droplets flow upwardly along the inner liner 68 in flow path 98. The liquid entrained in this gas will ordinarily be water with a variety of solutes and this liquid has a specific gravity which approximates that of water. In the case of stacks which are in use in many coal fired electrical generating plants, the liquid may be a very dilute sulfuric acid solution. The gas with entrained liquid then enters opening 94 beneath the inward overhang of the upper roof section 78 in flow path 100 which extends outwardly between the lower gutter section 76. The gas then moves upwardly and outwardly to leave the assembly through top opening 96 to the atmosphere in flow path 102. Liquid particles formerly entrained with the gas stream will ordinarily be too heavy to follow flow path 102 to exit through opening 96 with the gas stream. Instead, these liquid particles will ordinarily follow flow path 104 to be collected and exit the lower gutter section 76 through moisture drain 80 to drain to the space between the outer concrete stack shell 66 and the inner brick liner 68. Preferably at least some of the liquid droplets entrained with the gas stream this way will have a size greater than 250 microns.

It will be understood that while the liquid collection unit described herein is described as being positioned at the top of the stack, that it would be possible, within the scope of this invention, to position the liquid collection unit at an intermediate position between the top and the base of the stack. Such an intermediate positioning of the liquid collection unit might be particularly desirable in the case of new construction. When an existing stack is retrofitted with a liquid collection unit, however, it would ordinarily be preferred to position the liquid collection unit on the top of the stack.

Tests on and Modelling of System Components

1. Modeling of the Generation of a Swirl with an Impeller

Computational Fluid Dynamic (CFD) modelling for a 800 foot stack on a coal fired electrical generating plant for the installation of a 42 ft. diameter turning vane roughly 200 ft. from the stack exit demonstrated that a swirl component of about 67% of the axial velocity could be generated without imposing excessive pressure drop. This swirl was sufficient in magnitude to force virtually all large water droplets less than 250 microns to the stack wall prior to exit from the stack. In addition to the turning vane, ten rings of horizontal liquid collectors would be installed on the wall to both collect water draining down the wall and create a thick, low velocity boundary layer on the stack wall to mitigate droplets from being carried upward near the wall. The separator would be located a little over two diameters downstream of the Continuous Emissions Monitoring (CEM) ports. One of the significant drivers was that the separator had to be designed to prevent interference with the gas flow pattern at the CEM ports.

2. Modeling of the Generation of a Swirl at the Transition of the Breaching Ducts Into the Stack Generating swirl at the breaching duct transition into the stack was alternatively modeled. The existing configuration imposed a kidney shaped recirculating pattern across the cross section of the flow. In addition, the pattern shifted depending on which absorber modules were in service. In order to eliminate this transverse recirculation pattern, it was proposed that flow straighteners be installed at the bottom of the stack. While uniform, straight flow without a transverse recirculating patterns was considered most desirable, a uni-directional swirl was considered acceptable so long as the tangential (swirl) vector component produces no more than a 20 degree "yaw" angle relative to the axial vector at the CEM, located approximately twelve stack diameters downstream. With a mean stack velocity of about 50 ft./sec., it was determined that there was a maximum average swirl of about 18 ft./sec.

3. Droplet Testing

Droplet testing was conducted on stacks before the invention was installed. This testing demonstrated that droplets were not concentrated near the wall but rather well distributed. It was observed that water that strikes the wall would deposit and/or shatter. It was also determined a portion of this water would be re-entrained into the gas stream. With the proposed swirl generated at the bottom of the stack, it was also determined water droplets would be forced to the wall and forced stay on or near the wall throughout the length of the stack. Rather than installing a system of liquid collectors, a "choke" collector ring (inverted gutter), was found to be as effective in collecting the droplets as they reach the top of the stack. Due to the surface irregularities of the stack wall, it was hypothesized that a water droplet could be deposited and re-entrained many times as it "creeps" its way up the stack near the wall.

4. Swirl Component Decay Modeling

This stack model along with a more detailed breaching duct vane model and two liquid collector alternative models were developed as a design tool to help eliminate the sporadic liquid carryover that is discharged by many stacks. It was determined that by installing turning vanes in the breaching ducts and a means for liquid collection on the walls, a 800 ft. tall wet stack could be, in effect, be turned into a giant low velocity liquid/gas cyclone.

A stack Computational Fluid Dynamics (CFD) Fluent model was developed in order to determine whether sufficient swirl could be imposed (and maintained up the stack's length) on the flow to force and keep both absorber carry-over and stack liner condensing droplets on the wall. At the same time, the swirl component had a measurement limitation of a 200° yaw angle (or the equivalent of 20 ft./sec. at full load) at the (GEM) elevation, i.e., the average swirl velocity would not exceed 20 ft./sec. at the CEM elevation. This particular model assumed that four absorbers were in operation and the unit would run at full load. Five absorber operation was considered the norm, but a four module operation was at times considered necessary and presented a bounding case for normal velocity component entering the stack.

Under five module operation, the stack model results demonstrated that an effective 25° turning vane was required in order to achieve the maximum amount of swirl without exceeding the 20° yaw angle at the CEM elevation. Even though, four module operation required an angle of only 22° to achieve the CEM elevation swirl velocity limit, it should be understood that this fluent model was only a calculation with best assumptions incorporated. Swirl decay was directly impacted by radial surface roughness/discontinuities (along both tangential and axial directions) which is unknown to a large extent. The modelling incorporated a relative surface roughness of the brick liner which could be high or low and which could vary from one actual stack to another. It was believed that a 25 degree spin could be preferred even though this angle might be theoretically too severe when operating with four modules. If actual practice indicated that this angle was too sharp an angle, it was determined that vane surface would be removed. It was determined that, as a general rule, the direction of rotation would be counterclockwise when looking down at the stack. (This model used the opposite direction; the convention was adopted subsequent to the models completion). The model also demonstrated that all the droplets (250 microns and larger) which entered the stack from the absorbers were forced to the liner within the lower half of the stack's height. The results of this model and models of the liquid collector alternatives also indicated that the swirl is sufficient, up through to the stack exit, to keep the droplets effectively at the wall. Some of the water that strikes the wall drains down along the wall to drains located in the floor of the stack.

5. Vane Pressure Modelling

This model was developed to determine the effectiveness of turning vanes in imposing the required tangential (swirl) component. Additionally, this model determined the static pressure loading of the flow on the turning vanes. That model determined the resulting forces, moments, stresses and harmonics on the turning vanes to help develop a durable vane design.

The stack model results indicated that an effective 25 degree turning vane should be used for flow design purposes. Conservatively, a 30 degree vane angle was used in the model to determine loadings on the vane surfaces. The model results indicated that installing six 2 ft. wide by 36 ft. tall vanes, evenly distributed across the exit of the breaching duct and angled at 30 degrees from the centerline of incoming flow was sufficient to effectively impose virtually a 30 degree tangential velocity component across the entire incoming flow cross-section. Additionally, the model showed a non-uniform pressure load distribution on each blade, the average of which was about 1.2 $H_2O$ (0.042 psid). Because the pressure distribution was non-uniform, as anticipated, the flow also exerted a moment on the blades. As stated above, the resulting stresses were determined using a finite element model.

6. Droplet Separation Modelling

It was determined that water will flow down on smooth vertical walls so long as the upward free stream velocity was below 60–70 ft./sec. The prior art indicates that the critical re-entrainment velocity for brick liners with ¼" offsets approached the terminal velocity of large droplets that are flattened out, i.e., about 25 ft./sec. This terminal velocity corresponded to a spherical droplet of about 2000 microns (slightly over ¹⁄₁₆" in diameter). In a brick stack operating at a nominal velocity of 50 ft./sec., water would drain down the brick surface until the water comes to a discontinuity where it would drip (within the boundary layer) or be sheared off (due to turbulence fluctuations or local surface configuration upstream of the drip).

A current breaching arrangement (without turning vanes) caused a double vortex to form. Water droplets that drip off the wall are centrifuged back to the wall around much of the stack circumference. However, one location existed in particular wherein the outer reaches of the vortices meet. Here the droplets could be pulled directly into the main gas flow. In addition, the action of the opposing double vortex was found to cause these vortices to become negligible in the upper reaches of the stack. Droplet testing also indicated that droplets are present across the stack cross section. The testing also showed that the majority of these droplets are within the 500–1000 micron diameter size range. Testing has shown that virtually all are smaller than 3000 microns.

Spinning the flow from the bottom of the stack in one uniform vortex was determined to cause virtually all the droplets, 250 microns and greater, carried over from the absorbers and breaching ducts to be spun out to the wall. Droplets condensed on the wall should theoretically stay on or near the wall. Fluent modelling indicated that droplets greater than 300 microns tended to cling to the wall and migrate downwardly. Small droplets clung to the wall and migrated upwardly. The flow was turbulent and localized fluctuations/eddies were found to have localized impacts as flow moves up the stack. The model also indicated that the swirl decay is gradual with one vortex, and the swirl velocity at the top of the stack was still about half the strength it was above the breaching ducts.

This model suggested that two alternatives would be possible to collect the liquid migrating upward. In a first alternative an inverted gutter was used as a liquid/gas separation chamber. It was installed on top of the brick liner at the exit of the stack. In a second alternative uses two gutters were installed 20 ft. and 40 ft. below the exit of the stack. Additionally, an 18 in. transition piece was installed below the lower gutter and a 6 ft. choker ring was installed at the stack exit. This alternate relied on the gutters and upper ring to establish a thick low velocity boundary layer zone wherein the water drains down into the gutters once reaching this elevation.

This proposed liquid separator and collector was determined to be simpler and more forgiving in design, was lower in cost, was easier to maintain and possibly as effective as the prior art methods and apparatus for removing liquid from a gaseous stream in a stack.

Example of Actual Operation of the Entire System

1. Introduction

An actual test was conducted on the Unit 1 stack at the Gavin electrical power plant operated by American Electric Power located at Chesire, Ohio USA. Previous tests had been conducted on the Unit 2 at mist eliminator exits, stack breeching, and in the stack at two elevations, the 450 foot elevation and at the 819 foot elevation of the 830 foot stack. During the earlier tests, possible relationships between the droplet emissions and the number of scrubber modules and pumps in service were explored. The results of those tests, showed that the droplet concentrations were relatively insensitive to the number of modules and/or pumps in service although there were some indications of higher concentrations when only four modules were in service. However, a marked decrease in droplet concentrations was observed between the (CEM) level and the top of the stack. The annulus pressurization air was turned off for several days between the testing at the CEM level and the tip of the stack and remained off throughout the testing at the stack top during the earlier tests. It was speculated that much of the difference in droplet concentration may have been the result of turning the pressurization air off. The effect of the pressurization air was explored further in other prior tests which indicated that droplet emission rates were higher with the fan on than when the fan was off. By the term "modules" what is meant is conventional scrubber modules which are commonly used on stacks in coal fired electrical generating plants.

In this latest test, measurements were made at the top of the Unit 1 stack without annulus pressurization. Testing was done at two conditions, which were five modules in service and four modules in service. Testing with the annulus fan on was to be done as well.

2. Measurement Method

Droplets were measured with a Video Droplet Analyzer (VDA) developed at and is available from Southern Research Institute of Birmingham, Ala., USA for studies of scrubber mist eliminator performance. The VDA used on-the-fly image analysis to detect and measure the diameters of all in-focus droplets that are entirely within the field of view of the camera in each video frame. The camera operated at a frame rate of 60 frames per second. Illumination was provided by a 0.5 microsecond flash-duration strobe lamp that is synchronized to fire immediately before the start of each video frame. Counts of measured droplets were accumulated in 160 size channels. These size channels were each 33 $\mu$m wide as the system was configured for this test. The size range spanned by the VDA system for the Gavin tests was thus 33 $\mu$m to 5280 $\mu$m.

The size of the view volume in which droplets were measured by the VDA were set by two factors. The first was the focal length of the lens used for imaging the droplets as this sets the field width and height (10.4 mm by 8 mm in the configuration used for these tests.) The second factor was the depth-of focus, which varies with droplet size. A signal related to image sharpness was generated for each image on each video scan line that intercepts it. A discriminatory threshold was set which used this signal to reject images that were out of focus. For this test any image was rejected for which the measured size would have been in error by the greater of 33 $\mu$m or 10 percent of its diameter. That is, the maximum error for droplets smaller than 330 $\mu$m was 33 $\mu$m while the maximum error for droplets larger than 330 $\mu$m was ten percent of the measured size. A calibration curve providing depth-of-focus versus droplet size was generated in the laboratory using glass beads and paint spots of known sizes mounted on microscope slides prior to departure for any test in which the VDA was to be used. This calibration was sensitive to the illumination intensity; consequently the signal level for the video camera was monitored continuously during operation of the VDA and the intensity was adjusted if it departed from the value used when doing the laboratory calibrations of the system. In addition, spot checks were made of the depth-of-focus at one or more selected sizes immediately before and after completion of each VDA measurement session to ensure that the system operated as intended during the test.

The VDA system measured the concentration at each traverse point independently. However, these concentrations had to be weighted in proportion to the gas velocities at the traverse points to arrive at a concentration representative of the total flow through the duct, and to calculate carryover/carry-up rates. Consequently, a velocity traverse of the duct had to be made in conjunction with each droplet concentration traverse. The velocity measurements used in analyzing the Gavin VDA data were made using a conventional "S-type" pitot tube.

The VDA and pitot measurements were made at the locations called for by standard traverse patterns used to measure droplet concentrations and gas velocities over the selected sampling planes. At the stack and mist eliminator exit transform locations the traverses were made by suspending the probe (VDA or pitot) from cable stretched along diameters of the flue between pairs of ports on opposite sides of the flue. For the 42-foot diameter stack flue at Gavin Unit 1 a twenty-four point traverse was made with the points located at distances of 10", 2'–10", 5', 7'–5", 10'–6", and 14′–11″ from the stack walls along four radii at 90 degrees to one another. In addition, measurements were also made at the center of the flue were made to help define the shape of the droplet concentration profile.) Measurement times of four minutes at each traverse location were used at the stack locations.

The data for each set of measurements was stored as independent records in computer files. Each record contains the number of droplets counted in each of the 160 individual size channels together with identifiers for the travers point at which that data set was obtained and the time at which the measurement at that point ended.

3. Test Procedure

The VDA system calibration was checked, adjusted as needed, and verified prior to the start of the test. The result of the calibration verification was satisfactory. A minimum of 10 minutes of warm-up time was allowed after the VDA probe was initially inserted into the duct to allow it to equilibrate at the flue gas temperature before staring to take data. A velocity traverse was made between the two droplet traverses.

Measurement of the angle of cyclonic flow was attempted, however, the flow was too turbulent to permit measurement of the flow angle with any reliability. Visual observations of the flow near the sampling ports suggested that the angle was between 15 and 30 degrees from vertical.

4. Results and Discussion

Figure 3:
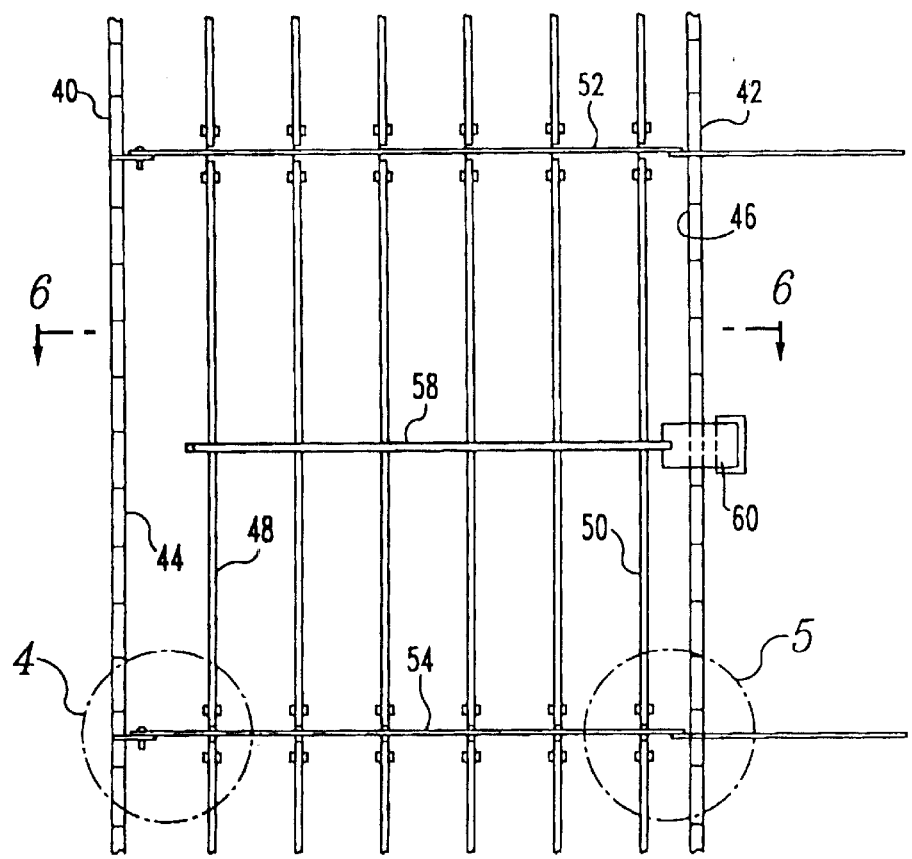
FIG. 3 is a detailed view of area 3 in FIG. 2.
Figure 4:
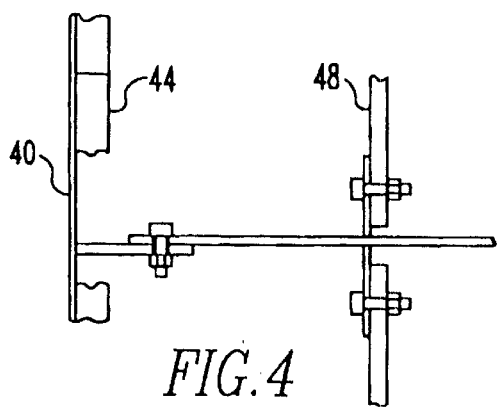
FIG. 4 is a detailed view of area 4 in FIG. 3.
Figure 5:
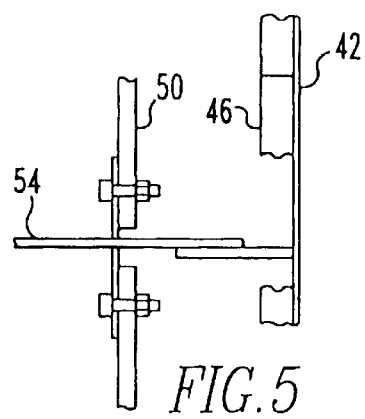
FIG. 5 is a detailed view of area 5 in FIG. 3.
Figure 6:
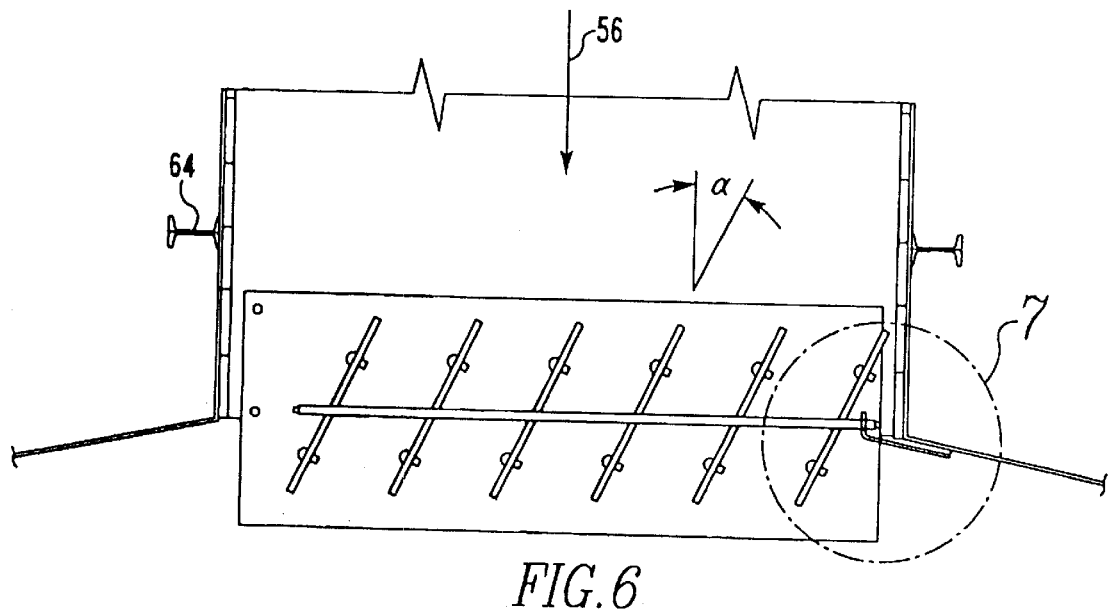
FIG. 6 is a cross sectional view through 6—6 in FIG. 3.
Figure 7:
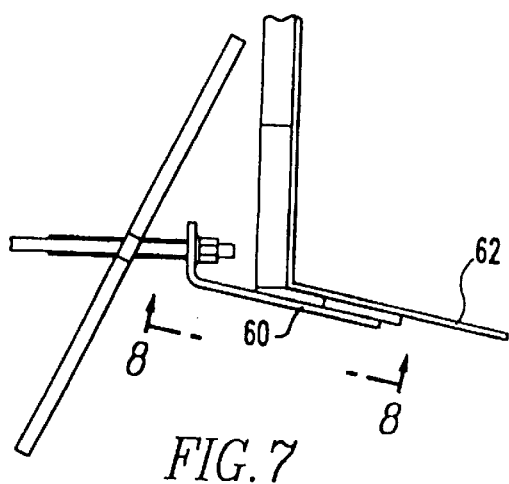
FIG. 7 is a detailed view of the area in circle 7 in FIG. 6.
Figure 8:
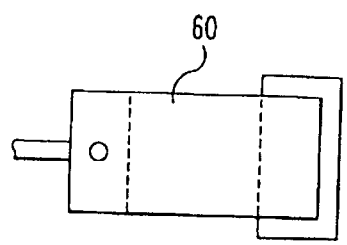
FIG. 8 is a view from 8—8 in FIG. 7.
Figure 9:
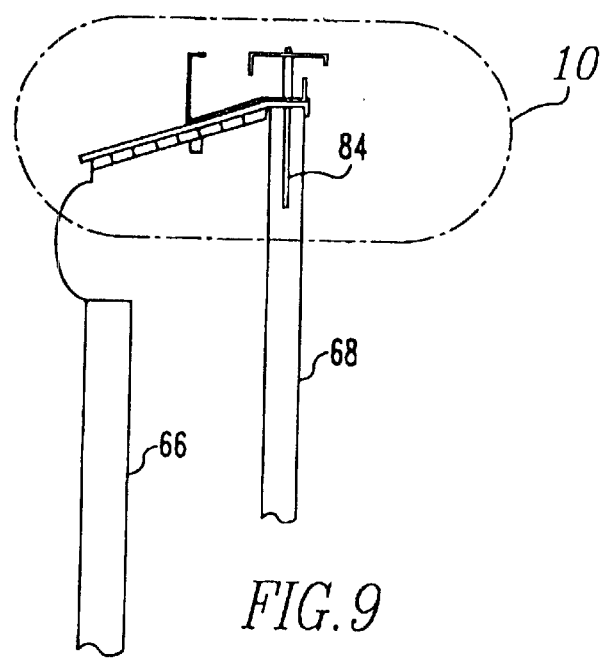
FIG. 9 is a cross sectional view of the top of the stack shell and liner of the stack shown in FIG. 1 showing a preferred embodiment of the stack cap collector feature of the apparatus of the present invention.
Figure 13:
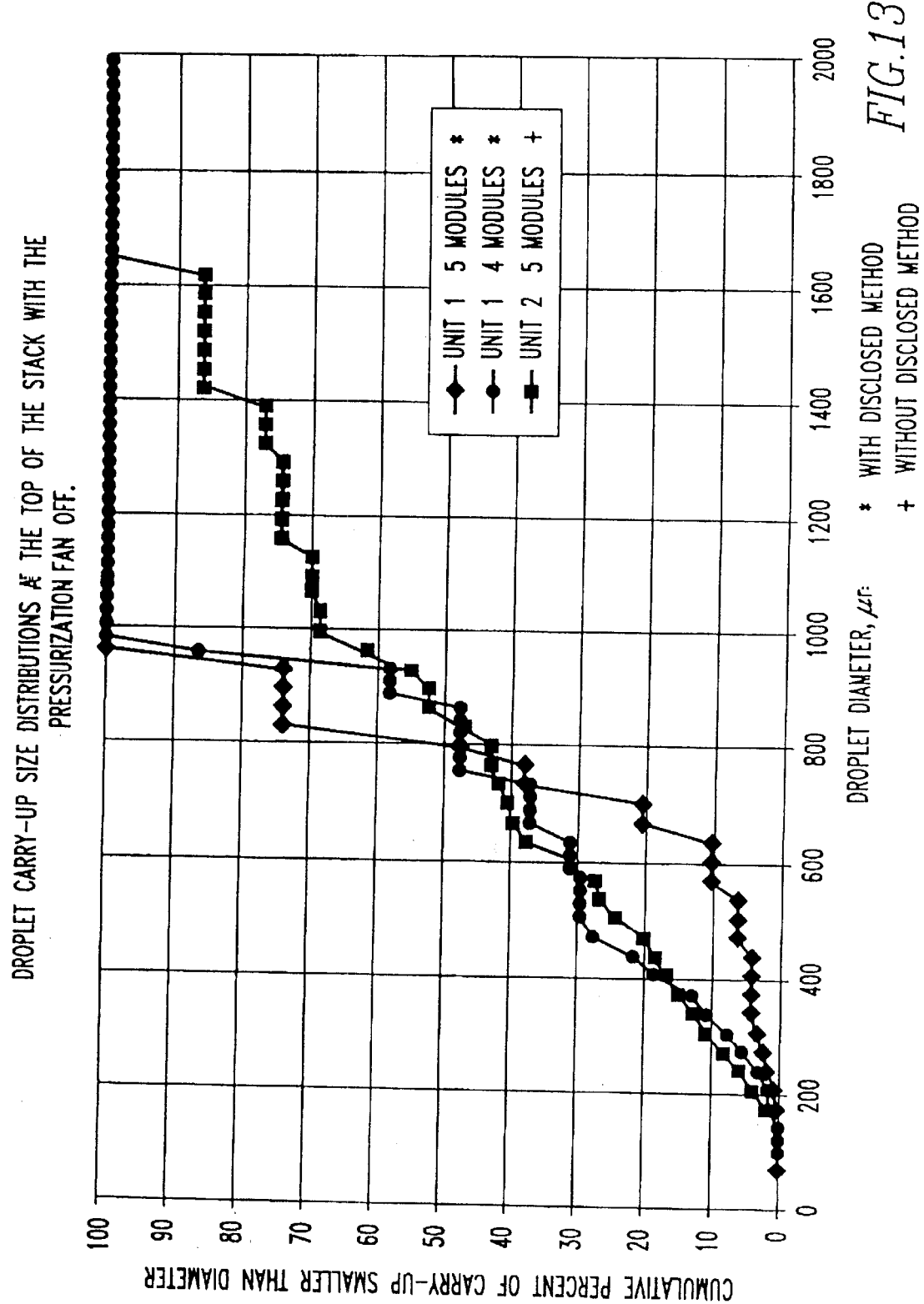
FIG. 13 is a graph showing droplet carry-up size distributions at the top of the stack with the distribution fan off for the example described herein.
Figure 14:
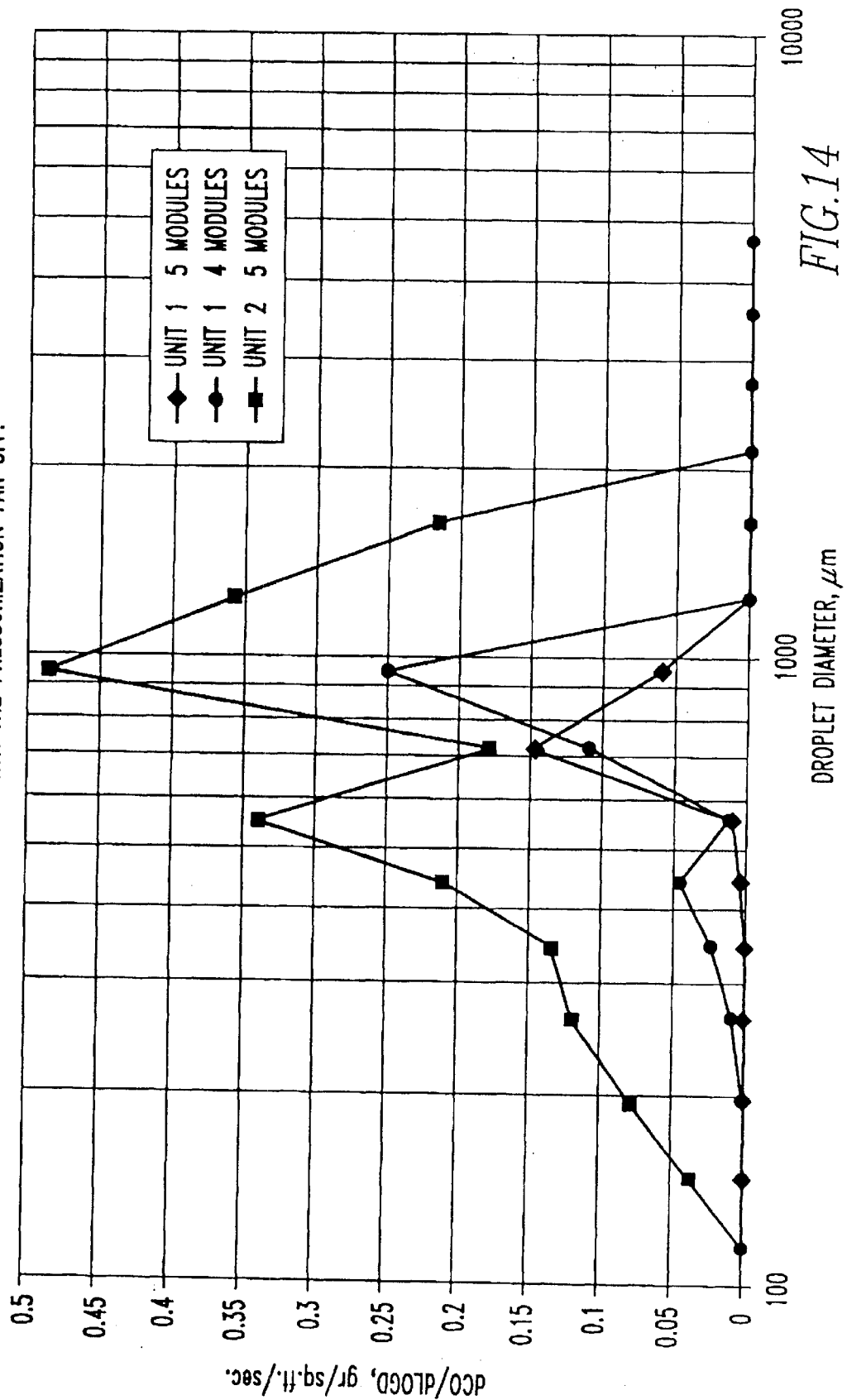
FIG. 14 is a graph showing droplet carry-up rate versus droplet diameter at the top of the stack with the pressurization fan off for the example described herein.
Figure 15:
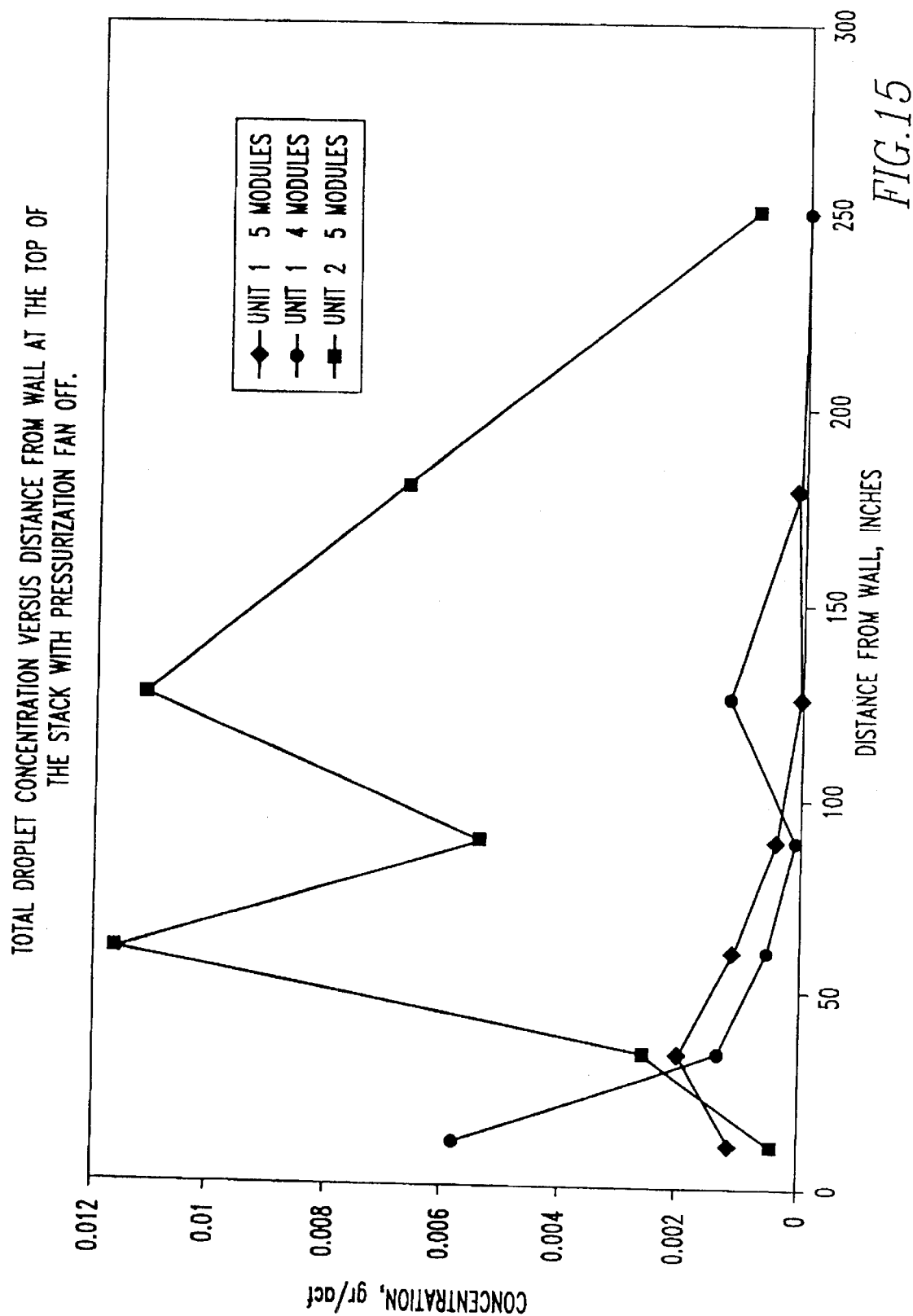
FIG. 15 is a graph showing total droplet concentration versus distance from the wall at the top of the stack with the pressurization fan off for the example described herein.

Results of the individual VDA traverses are summarized in Table 1. This table provides information on the scrubber setup during each test, the gas flow in the flue, the total liquid transport rates, the mass median diameters of the droplets, and the sizes of the largest droplets measured during each test. (Half of the total mass of the droplets is contained in sizes larger than the mass median diameter (MMD) and half in droplets smaller than the mass median diameter.) The droplet size distributions at the two conditions are shown in two formats in FIGS. 13 and 14. FIG. 13 shows the results in terms of the percentages by weight (or volume) contained in droplets smaller than any given diameter. FIG. 14 shows carry-up/carryover rates in grains per square-foot per second versus droplet diameter for Unit 1 (5 modules) and Unit 2 (4 modules) operating with the invention. The area under the curves between any two diameters in FIG. 14 equals the total carry-up rate for droplets with sizes between the two selected diameters. Results for the Unit 2 stack top test with five modules in service from the previous tests are included in the figures for comparative purposes. The spatial distribution of the droplets was quite different in these tests as compared to the previous tests on Unit 2 as illustrated in FIG. 3. Again, data from the 1998 tests on Unit 2 are included for comparative purposes.

Overall emission rates were found to be dramatically lower during these tests than in the previous tests on Unit 2. The emission rate for droplets larger than 100 $\mu$m under similar conditions with five modules in service was 23 pounds per hour on this occasion compared to 178 pounds per hour for Unit 2. The rate for Unit 1 increased to 39 pounds per hour when only four scrubber modules were in service.

The results obtained with four modules in service are based on an incomplete traverse but are believed to be reasonably reliable. After slightly more than three-quarters of the traverse had been completed at that condition a problem in the VDA hardware resulted in the loss of video to the analyzer. Severe plume downwash the following day precluded further testing even had the VDA problem been resolved. Although only three-quarters of the traverse had been completed, no systematic differences had been noted in results from the different quadrants during the previous tests, so the results from this incomplete test are believed to provide reasonably good indications of the droplet carry-up rate at the time.

The results of the velocity traverse are provided in Table 2. The pitot measurements indicated that the velocity at the center of the flue was zero. The average velocities, uncorrected for cyclonic flow angle, are shown plotted verses distance from the flue wall in FIG. 16. Assuming the cyclonic flow angle to be 30 degrees, the vertical components of the velocities would be 13% lower than those indicated in FIG. 16. The velocities used in the droplet emission rate calculations were reduced accordingly.

Qualitatively the method of this invention virtually eliminated droplets falling from the stack plane around the plant and neighboring sites.

TABLE 1

Results of Droplet Tests at Gavin Plant Unit 1

| Level | Number of Modules | Fan | Gas Flow, kacfm | Gas Temp., Deg. F. | Carry-up Rate lb/hr | MMD $\mu$m | Max. Diameter $\mu$m |
|---|---|---|---|---|---|---|---|
| Top | 5 | Off | 3715 | 133 | 0.046 | 800 | 1150 |
| Top | 4 | Off | 3715 | 133 | 0.078 | 850 | 1000 |

TABLE 2

Velocity Traverse at the Top Level of the Unit 1 Stack

| % $O_2$: | | | AMB PRESS, in. Hg: | 28.78 | PITOT CAL: | 0.79 |
| % $CO_2$ 12.0 | 7.8 | % $H_2O$ | STACK dP, in. $H_2O$: | 0.0 | DUCT AREA, ft2: | 1385.4 |

Cyclonic Flow Angle, degrees: 30

| | Port 1, Near Side | | Port 1, Far Side | | Center | |
|---|---|---|---|---|---|---|
| | VEL P | TEMP | VEL P | TEMP | VEL P | TEMP |
| POINT 1 | 0.93 | 133 | 0.5 | 133 | 0 | 133 |
| POINT 2 | 1.1 | 133 | 0.8 | 133 | | |
| POINT 3 | 1.1 | 133 | 0.9 | 133 | | |
| POINT 4 | 1.1 | 133 | 0.8 | 133 | | |

TABLE 2-continued

| | VEL P | TEMP | VEL P | TEMP | VEL P | TEMP |
|---|---|---|---|---|---|---|
| POINT 5 | 0.6 | 133 | 0.75 | 133 | | |
| POINT 6 | 0.25 | 133 | 0.45 | 133 | | |

| | Port 2, Near Side | | Port 2, Far Side | | Center | |
|---|---|---|---|---|---|---|
| | VEL P | TEMP | VEL P | TEMP | VEL P | TEMP |
| POINT 1 | 0.8 | 133 | 0.68 | 133 | 0 | 133 |
| POINT 2 | 1.0 | 133 | 1.1 | 133 | | |
| POINT 3 | 1.1 | 133 | 1.2 | 133 | | |
| POINT 4 | 0.95 | 133 | 1.15 | 133 | | |
| POINT 5 | 0.6 | 133 | 1.15 | 133 | | |
| POINT 6 | 0.1 | 133 | 0.9 | 133 | | |

Computed Velocity Data

| | Port 1, Near Side | | Port 1, Far Side | | Center | |
|---|---|---|---|---|---|---|
| | Vgas | TEMP | Vgas | TEMP | Vgas | TEMP |
| POINT 1 | 55.7 | 133 | 40.9 | 133 | 0.0 | 133 |
| POINT 2 | 60.6 | 133 | 51.7 | 133 | | |
| POINT 3 | 60.6 | 133 | 54.8 | 133 | | |
| POINT 4 | 60.6 | 133 | 51.7 | 133 | | |
| POINT 5 | 44.7 | 133 | 50.0 | 133 | | |
| POINT 6 | 28.9 | 133 | 38.8 | 133 | | |
| AVERAGE | 51.9 | 133 | 48.0 | 133 | | |

| | Port 2, Near Side | | Port 2, Far Side | | Center | |
|---|---|---|---|---|---|---|
| | Vgas | TEMP | Vgas | TEMP | Vgas | TEMP |
| POINT 1 | 51.7 | 133 | 47.6 | 133 | 0.0 | 133 |
| POINT 2 | 57.8 | 133 | 60.6 | 133 | | |
| POINT 3 | 60.6 | 133 | 63.3 | 133 | | |
| POINT 4 | 56.3 | 133 | 62.0 | 133 | | |
| POINT 5 | 44.7 | 133 | 62.0 | 133 | | |
| POINT 6 | 18.3 | 133 | 54.8 | 133 | | |
| AVERAGE | 48.2 | 133 | 58.4 | 133 | | |

| | | | |
|---|---|---|---|
| AVG STACK VELOCITY (raw), ft/s = | 51.6 | GAS VOL FLOW, kacfm: | 4290 |
| AVG STACK TEMPERATURE, F. = | 133 | GAS VOL FLOW, kdscfm: | 3049 |
| AVG SQRT (VELp) = | 0.8932 | GAS VOL FLOW, kscfm wet: | 3674 |
| Angle Corrected Average Velocity: | 44.7 | GAS VOL FLOW, kacfm: | 3715 |
| | | GAS VOL FLOW, kdscfm: | 2641 |
| | | GAS VOL FLOW, kscfm wet: | 3182 |

Other associated preferred aspects of wet stack design are well known to those skilled in the art. Such aspects of wet stack design are disclosed, for example, in *Web Stacks Design Guide,* published by Burns & McDonnell Engineering Company of 4800 East 63$^{rd}$ Street, Kansas City, Mo. 64130, USA in November, 1996, the contents of which are incorporated herein by reference.

It will be appreciated that a method and apparatus has been described which efficiently and cost effectively removes liquid entrained in a stack gas stream and which prevents liquid droplets from falling from the stack plane into areas adjacent the stack.

Accordingly, the improved STACK LIQUID SEPARATOR AND METHOD OF USE apparatus is simplified, provides an effective, safe, inexpensive, and efficient device which achieves all the enumerated objectives, provides for eliminating difficulties encountered with prior devices, and solves problems and obtains new results in the art.

In the foregoing description, certain terms have been used for brevity, clearness, and understanding; but no unnecessary limitations are to be implied therefrom beyond the requirement of the prior art, because such terms are used for descriptive purposes and are intended to be broadly construed.

Moreover, the description and illustration of the invention is by way of example, and the scope of the invention is not limited to the exact details shown or described.

Having now described the features, discoveries, and principles of the invention, the manner in which the STACK LIQUID SEPARATOR AND METHOD OF USE is constructed and used, the characteristics of the construction, and the advantageous new and useful results obtained; the new and useful structures, devices, elements, arrangements, parts, and combinations are set forth in the appended claims.

What is claimed is:

1. An apparatus for removing a liquid entrained in a gas stream in a stack having a base and a top comprising:
    at least one duct having a longitudinal axis entering the stack adjacent said base and at least one vertical vane disposed at an angle of from 15° to about 35° relative to the longitudinal axis of the duct; and
    a liquid collecting means mounted on the stack.

2. The apparatus of claim 1 wherein at least one duct is adjacent the base.

3. The apparatus of claim 2 wherein there are a plurality of ducts and the base has first and second opposed sides and the ducts are all positioned on only one of said opposed sides.

4. The apparatus of claim 3 wherein there are from 4 to 6 ducts.

5. The apparatus of claim 1 wherein there are a plurality of vertical vanes.

6. The apparatus of claim 1 wherein the vane is positioned relative to the longitudinal axis at an angle of about 25°.

7. The apparatus of claim 1 wherein the liquid collecting means comprises a gas enclosing structure with a gas stream input opening.

8. The apparatus of claim 1 wherein the means for collecting liquid comprises:
   a lower concave gutter section;
   an upper roof section superimposed over the concave gutter section;
   a gas stream intake opening; and
   a liquid drain.

9. The apparatus of claim 1 wherein the liquid collection means is mounted on the top of the stack.

10. An apparatus for removing a liquid entrained in a gas in a stack having a base, a top and opposed first and second sides comprising:
   a plurality of ducts each having a longitudinal axis and positioned on said stack at the base, each of said ducts having a plurality of vertical vanes disposed at and angled to the longitudinal axis of the duct; and
   a liquid collecting system comprising a gas enclosing structure with a gas stream input opening.

11. An apparatus for removing a liquid entrained in a gas in a stack having a base, a top and opposed first and second sides comprising:
   a plurality of ducts each having a longitudinal axis and positioned on said stack at the base, each of said ducts having a plurality of vertical vanes disposed at an angle to the longitudinal axis of the duct; and
   a liquid collecting system comprising a lower concave gutter section; an upper roof section superimposed over the concave gutter section; a gas stream intake opening; and a liquid drain.

12. An apparatus for removing a liquid entrained in a gas stream in a stack comprising:
   means for imparting a swirling direction to the gas stream; and
   means for collecting liquid from the gas stream which is mounted on the top of the stack.

13. The apparatus of claim 12 wherein the stack has a base and the means for imparting a swirling direction to the gas stream is mounted adjacent the base of the stack.

14. The apparatus of claim 12 wherein the stack has a radius and the means for imparting a swirling direction to the gas stream is a means for introducing a fluid into the stack in a non-radial direction.

15. A method of removing a liquid entrained in a gas stream moving in a generally upward direction from a base to a top of a stack comprising the steps of imparting a swirling direction to the gas stream and then recovering at least some of the liquid from the gas stream at the top of the stack.

16. The method of claim 15 wherein the swirling direction is imparted to the gas stream adjacent the base of the stack.

17. The method of claim 15 wherein the liquid is water having one or more solutes.

18. The method of claim 15 wherein the liquid is included in a plurality of particles, and at least some of said particles have a dimension greater than 250 microns.

19. The method of claim 15 wherein said swirling direction is imparted by an impeller.

20. The method of claim 15 wherein the stack has a radius and said swirling direction is imparted by introducing a fluid into the stack in a non-radial direction.

21. The method of claim 15 wherein the liquid is removed from the gas stream in a gas enclosing structure with a gas stream input opening.

22. The method of claim 21 wherein the gas enclosing structure has a gas stream output opening positioned in outward relation to the gas stream input opening and a liquid drain positioned in outward relation to the gas stream input opening, and said output opening is positioned in elevated relation to said drain, wherein said gas stream enters the gas enclosing structure and divides into an upwardly directed stream substantially free of entrained liquid which escapes the gas enclosing structure through the gas stream output opening and a downwardly directed stream containing liquid droplets which are collected and released from the gas enclosing structure through the drain.

23. An apparatus for removing a liquid entrained in a gas stream in a stack having a base and a top comprising:
   at least one duct having a longitudinal axis entering the stack adjacent said base and a plurality of vanes disposed at an angle to the longitudinal axis of the duct; and
   a liquid collecting means mounted on the stack.

24. The apparatus of claim 23 wherein the vertical vanes are equipped with a horizontal stiffening rod.

25. The apparatus of claim 23 wherein the vertical vanes are disposed at an angle of from about 15° to about 35° relative to the longitudinal axis.

26. The apparatus of claim 23 wherein the vanes are positioned relative to the longitudinal axis at an angle at which turbulence adjacent said vanes is minimized.

27. The apparatus of claim 23 wherein the vanes are disposed at an angle to the longitudinal axis of the duct and the angle at which the vanes are positioned relative to the longitudinal axis of the duct is adjustable.

28. An apparatus for removing a liquid entrained in a gas stream in a stack having a base and a top comprising:
   a plurality of ducts located adjacent the base, each of the ducts having a longitudinal axis entering the stack adjacent said base and at least one vertical vane disposed at an angle to the longitudinal axis each of said ducts;
   said base having first and second opposed sides with said ducts being positioned on only one of said opposed sides; and
   a liquid collecting means mounted on the stack.

29. An apparatus for removing a liquid entrained in a gas stream in a stack having a base and a top comprising:
   at least one duct having a longitudinal axis entering the stack adjacent said base and at least one vertical vane disposed at an angle to the longitudinal axis of the duct; and
   a liquid collecting means comprising a gas enclosing structure with a gas stream input opening mounted on the stack.

30. An apparatus for removing a liquid entrained in a gas stream in a stack having a base and a top comprising:
   at least one duct having a longitudinal axis entering the stack adjacent said base and at least one vertical vane disposed at an angle to the longitudinal axis of the duct; and
   a liquid collecting means mounted on the stack comprising a lower concave gutter section, an upper roof section superimposed over the concave gutter section, a gas stream intake opening, and a liquid drain.

31. The apparatus of claim 30 wherein there is an upper gas stream exit opening.

32. The apparatus of claim 31 wherein the gutter section has an inner side and an outer side, and the gas stream intake opening is adjacent and said inner side, and the gas stream exit opening is adjacent said outer side of the gutter section.

33. The apparatus of claim 32 wherein the liquid drain is positioned adjacent the outer side of the gutter section and beneath the gas stream exit opening.

34. The apparatus of claim 33 wherein the upper roof section extends radially inwardly to overhang the inner side of the gutter and the gas stream intake opening.

35. The apparatus of claim 34 wherein an inner flange extends downwardly from the upper roof section.

36. The apparatus of claim 30 wherein the stack comprises a stack shell and a liner positioned radially inwardly from said stock shell, and the liquid collecting means includes a cap extending downwardly and outwardly between the liner and a stack shell.

37. An apparatus for removing a liquid entrained in a gas stream in a stack having a base and a top comprising:
   at least one duct having a longitudinal axis entering the stack adjacent said base and at least one vertical vane disposed at an angle to the longitudinal axis of the duct; and
   a liquid collecting means mounted on top of the stack.

38. A method of removing a liquid entrained in a gas stream moving to a stack through a duct and then in a generally upward direction from a base to a top of a stack comprising the steps of imparting a swirling direction to the gas stream as it enters the stack from the duct by passing the gas stream past a vertical vane disposed at an angle of from 15° to about 35° to a longitudinal axis of the duct; and then recovering at least some of the liquid from the gas stream at a position adjacent the stack.

39. The method of claim 38 wherein the liquid is recovered from the gas stream at the top of the stack.

40. The method of claim 38 wherein the liquid is recovered from the gas stream at a position between the top and the base of the stack.

41. The method of claim 39 wherein said fluid is introduced in at least one duct having a radial longitudinal axis and said duct has at least one vertical vane disposed in angular relation to the longitudinal axis of the duct.

42. A method of removing a liquid entrained in a gas stream moving into a stack through a duct and then in a generally upward direction from a base to a top of a stack comprising the steps of imparting a swirling direction to the gas stream as it enters the stack from the duct by passing the gas stream past a plurality of vertical vanes disposed at an angle to a longitudinal axis of the duct; and then recovering at least some of the liquid from the gas stream at a position adjacent the stack.

* * * * *